United States Patent
Missoli (10) Patent No.: US 9,630,020 B2
(45) Date of Patent: Apr. 25, 2017

(54) ELECTROMEDICAL DEVICE

(71) Applicant: MANTIS SRL, Castelnovo Ne' Monti Reggio Emilia (IT)

(72) Inventor: Franco Missoli, Buccinasco-Milano (IT)

(73) Assignee: MANTIS SRL, Castelnovo Ne' Monto (Reggio Emilia) (IT)

( * ) Notice: Subject to any disclaimer, the term of this patent is extended or adjusted under 35 U.S.C. 154(b) by 239 days.

(21) Appl. No.: 14/376,850

(22) PCT Filed: Feb. 12, 2013

(86) PCT No.: PCT/IB2013/000179
§ 371 (c)(1),
(2) Date: Aug. 6, 2014

(87) PCT Pub. No.: WO2013/121265
PCT Pub. Date: Aug. 22, 2013

(65) Prior Publication Data
US 2015/0005569 A1    Jan. 1, 2015

(30) Foreign Application Priority Data

Feb. 16, 2012   (IT) .............................. RE2012A0011

(51) Int. Cl.
*A61N 2/00*   (2006.01)
*A61H 15/00*  (2006.01)
(Continued)

(52) U.S. Cl.
CPC ............ *A61N 2/008* (2013.01); *A61H 9/0057* (2013.01); *A61H 15/0085* (2013.01); *A61N 2/02* (2013.01);
(Continued)

(58) Field of Classification Search
CPC .... A61H 2201/5005; A61H 2015/0014; A61H 2201/5082; A61H 15/0085;
(Continued)

(56) References Cited

U.S. PATENT DOCUMENTS 5,665,053 A  *  9/1997  Jacobs ................... A61H 7/008
                                                    601/123
2003/0032900 A1*  2/2003  Ella ........................ A61H 7/008
                                                    601/6

(Continued)

FOREIGN PATENT DOCUMENTS

JP   2008093345   4/2008
WO   2004023235   3/2004
(Continued)

*Primary Examiner* — Christine H Matthews
*Assistant Examiner* — Joshua D Lannu
(74) *Attorney, Agent, or Firm* — Mark M. Friedman (57) ABSTRACT

An electromedical device comprising an operating head which has a depression chamber provided with an opening and connected to a vacuum pump. A pair of rollers are placed in the depression chamber and are connected to an electrical motor for rotating the rollers. The electromedical device further comprises a generator of pulsed electric current and an electromagnetic transducer, which is connected to the generator such as to transform the pulsed electric current into a pulsed magnetic field that crosses the opening of the depression chamber.

13 Claims, 6 Drawing Sheets

(51) Int. Cl.
  *A61N 2/02* (2006.01)
  *A61H 9/00* (2006.01)
  *A61H 7/00* (2006.01)

(52) U.S. Cl.
  CPC .............. *A61H 2007/009* (2013.01); *A61H 2015/0014* (2013.01); *A61H 2201/10* (2013.01); *A61H 2201/5005* (2013.01); *A61H 2201/5048* (2013.01); *A61H 2201/5082* (2013.01)

(58) Field of Classification Search
  CPC ...... A61H 2007/009; A61H 2201/5048; A61H 9/0057; A61H 2201/10; A61N 2/008; A61N 2/02
  See application file for complete search history.

(56) References Cited

U.S. PATENT DOCUMENTS

2003/0073937 A1* 4/2003 Guitay .................. A61H 7/008
  601/6
2011/0009783 A1* 1/2011 Dverin .................. A61B 18/14
  601/137

FOREIGN PATENT DOCUMENTS

WO  2007019580  2/2007
WO  2011021184  2/2011

* cited by examiner

ELECTROMEDICAL DEVICE

TECHNICAL FIELD

The present invention relates to an electromedical device for treating the human body with the aim of obtaining a benefit of the cosmetic and/or medical type.

In particular, the present invention relates to an electromedical device for localised and non-invasive treatment of the human body, i.e. a device which acts from outside the body and is normally in contact with the skin.

BACKGROUND ART

As is known, numerous electromedical devices are at present available, for localised and non-invasive treatment of the human body, which are generally united by the fact of comprising an operating head (also known as a hand-piece) suitable for gripping by an operator and moved in contact with the skin of the patient at the zone to be treated.

Some of these devices can have the purpose of treating specific skin problems, or problems of the surface tissues of the human body, for example the epidermis and/or the skin. By way of example, these devices can be predisposed to facilitate stretching-out of wrinkles, elimination of adipose accumulations or lymphatic circulation, but also to facilitate the treatment of actual pathologies, such as for example varicose ulcers, phlebitic ulcers, arteriopathic ulcers, acne, burns, unhealed wounds and cellulite.

Other devices can be aimed at dealing with problems relating to the more internal organs of the human body, such as for example facilitating mending of bone fractures and/or enhancing the treatment of other pathologies such as arthritis, arthrosis, rheumatism, osteoporosis, pseudoarthritis, lumbago, periarthritis, sciatica, stiff neck, cervical arthrosis, paresis, muscular atrophy, pulmonary emphysema, hepatic failure and cirrhosis.

According to the particular aims, these electromedical devices are generally configured such as to apply a different type of treatment to the patient's body via the operating head, for example a massaging action, a magnetic field (magnetotherapy), electromagnetic waves or other treatments besides. A drawback of these electromedical devices consists however in the fact that there is a limit result in terms of effectiveness, requiring numerous and long sittings before any appreciable result is achieved.

DISCLOSURE OF THE INVENTION

An aim of an embodiment of the present invention is thus to resolve the above-mentioned drawback in the prior art, by making available an electromedical device for non-invasive treatment of the human body, which is more effective and therefore can require a shorter treatment time with respect to the known devices.

A further aim is to attained the above-mentioned aim with a solution that is simple, rational and relatively inexpensive.

These and other aims besides are attained with an embodiment of the invention having the characteristics recited in independent claim 1. The dependent claims delineate preferred and/or particularly advantageous aspects of the described embodiment of the invention.

In more detail, an embodiment of the invention discloses a device for treatment of the human body, comprising:

a depression chamber provided with an opening, which is destined to be applied to the patient such that a surface of the patient's body closes the opening, aspirating means connected to the depression chamber, such that when the depression chamber is closed by a surface of the body, the aspirating means can create internally thereof a certain degree of depression, i.e. an internal pressure that is lower than the ambient pressure, a pair of rollers suitable for at least partly delimiting the opening of the depression chamber, such as to be able to be in direction contact with the surface of the body closing the opening of the depression chamber, motor means suitable for rotating the rollers, a generator of pulsed electric current, and an electromagnetic transducer connected to the generator such as to transform the pulsed electric current into a pulsed magnetic field, the electromagnetic current being configured such that the flow of the pulsed magnetic field crosses at least the opening of the depression chamber, such as to be able to interest at least the surface of the body closing it.

Thanks to this solution, the body is initially subjected to an effective magnetotherapy treatment produced by the pulsed magnetic field, which can be exploited so as to obtain a multiplicity of analgesic effects and/or therapeutic effects in the treatment of various pathologies. By way of example, the action of the pulsed magnetic field can be effectively used such as to obtain a tissue anti-ageing action, beneficial effects on the nervous central and peripheral nervous system, positive influences of the bio-energetic type, soothing effects on inflammation, beneficial effects on the blood, on the bone tissue and the digestive apparatus.

At the same time, the suction effect generated by the depression chamber is such that the cutaneous surface closing the depression chamber is slightly raised between the two rollers, forming a fold that is similar to the one created by hand by a masseur during a massage. This action, together with the displacement of the device on the body of the patient, creates a massaging action which is known as endomassage or endodermic massage. This massaging action obtained effects similar to those of a draining massage or a manual lymphomassage, and is therefore very effective in facilitating the dissolving of the accumulations of fat and stimulating the lymphatic circulation. The negative pressure exerted by the aspiration, together with the positive pressure exerted by the rollers and the displacement of the device on the body, further create a mechanical stimulation with involves the anatomic structures underlying the fold. The main effects of this mechanical action are those of obtaining a restructuring of the connective tissue, a proliferation of chondrocytes in the cartilages, increase in blood profusion, blood flow and venous return, and an increase in the number of fibroblasts.

Numerous experiments have shown that this mechanical and massaging action also has the effect of increasing the analgesic and/or therapeutic effects of the pulsed magnetic field, obtaining a synergic effect which goes beyond a simple superposing of the two treatments.

In an aspect of the invention, the motor means of the above-delineated device can be configured such as to cause the rollers to roll in the same direction.

This aspect of the invention has the advantage of facilitating the movement of the electromedical device on the patient's skin, advantageously reducing the friction caused by the suction effect generated by the depression chamber, which might otherwise cause pain or in any case a certain degree of discomfort to the patient when the device was being moved about. In particular, the rotation velocity impressed on the rollers can be the same for both, or can be different, such that the difference of velocity of the two rollers contributes to creating the fold, adding to the suction effect generated by the depression chamber.

It is however possible that the motor means of the device can be configured such as to rotate the rollers in opposite directions, such as to further amplify the skin-raising effect mentioned above.

In a further aspect of the invention, at least one of the rollers of the device (or both) can be mounted mobile, such as to be able to vary the distance thereof with respect to the other roller, spring means being provided for maintaining the mounted roller mobile in a maximum distance position with respect to the other roller.

With this mobile mounting, when the fold forms, the rollers near one another in contrast with the spring means, such as substantially to follow and accompany the displacement of the patient's skin. This nearing therefore has the advantage of preventing the rollers from dragging on the skin, causing pain or in any case a certain discomfort for the patient.

In a further aspect of the invention, the pulsed electric current generator comprises an audio generator, for example a reader or multi-media reproduction device (radio, cd, mp3, etc.), and an amplifier connected to the audio generator and the electromagnetic transducer, such as to amplify an audio signal generated by the audio generator and transmit the amplified audio signal to the electromagnetic transducer.

In this way, the pulsed magnetic field generated by the electromagnetic transducer varies over time, following the progression of the pilot audio signal. The advantage of this solution is the great versatility of the device, which enables magnetic fields to be obtained which respond to the most different recordable audio signals and therefore reproducible with the audio generator, and pass from one to the other simply by changing the recording.

In an aspect of the invention, the audio signal transmitted to the electromagnetic transformer comprises a pulsed audio signal superposed on a stochastic audio signal.

In this way, the electromagnetic transducer is able to generate a magnetic field that is substantially made up of a combination of the pulsed magnetic field and a stochastic magnetic field, the effects of which superpose one another, generating a stochastic magnetic resonance phenomenon.

A stochastic magnetic field can be defined as a pulsed magnetic field, in which the frequency of the pulses varies repeatedly and randomly, giving rise to a sort of indistinct magnetic "noise".

Thanks to this stochastic resonance phenomenon a significant improvement in the effectiveness of the magnetotherapy treatment has been registered, which enables obtaining the same benefits that are obtainable with the traditional device, but in a shorter time and therefore with a smaller number and/or duration of the therapeutic sittings. All of this occurs without having to increase the amplitude of the pulses of the pulsed magnetic field, thus reducing the heating by Joule effect of the electromagnetic transducer, which otherwise might cause discomfort to the patient.

Naturally, in order to obtain these advantageous effects, the entity of the stochastic magnetic field, i.e. the level of magnetic "noise", has to be specially calibrated on the basis of the type of pathology under treatment, and on the basis of the characteristics of the pulsed magnetic field to which it is subjected.

In an aspect of the invention, the device can comprise a processor connected to the amplifier in order to regulate the power of the amplified audio signal from the amplifier.

In this way, it is advantageously possible to regulate the power of the pulsed magnetic field generated by the electromagnetic transducer and applied to the patient.

In a further aspect of the invention, the device can comprise a temperature sensor suitable for measuring the temperature of the electromagnetic transducer, which is configured such as to regulate the power of the audio signal amplified by the amplifier, as a function of the temperature measured by the temperature sensor.

Thanks to this solution, the processor is advantageous able to automatically regulate the power of the pulsed magnetic field, for example in such a way as to prevent irritations and scalding on the patient, which might be caused by an excessive heating of the electromagnetic transducer by Joule effect.

In a further aspect of the invention, the audio generator is further connected with a loudspeaker, for example a pair of earpieces, earphones or the like, for transforming an audio signal generated by the audio generator into an audible signal.

With this solution, the above-delineated device is advantageously able also to perform a music-therapy treatment, preferably contemporaneously with the endo-dermic massage and/or with magnetotherapy.

Music therapy is a complementary medical technique which uses music as a treatment tool and a way of maintaining a feeling of well-being, and is considered to be among the broadest definition of sound-therapy, in which the sounds are used to improve the psychological and physical conditions of individuals. In general, music influences the heartbeat, blood pressure, respiration and the levels of some hormones, such as endorphins.

Experiments have shown that the application of music therapy, following a suitable choice of the piece of music to be used (for example concerto K448 by Mozart), also has the effect of increasing the benefits generated by the massaging action and magnetotherapy, obtaining a synergic effect which goes beyond the mere combination of the effects of the single treatments.

In an aspect of the invention, the audio signal transmitted to the loudspeaker comprises harmonic components having a frequency comprised between 16 and 22 KHz.

This aspect of the invention has the advantage that the high-frequency sounds are able to obtain a Tomatis effect, i.e. they are stimulating for the brain, making it better able to concentrate, memorise, learn, while alleviating the sensation of weariness and depression.

In a further aspect of the invention, the audio generator is a multi-channel audio generator, which is connected with the electromagnetic transducer and with the loudspeaker in such a way that a first audio channel, for example channel R, is transmitted to the electromagnetic transducer and a second audio channel, for example channel L, is transmitted to the loudspeaker.

This aspect of the invention has the advantage of providing a very simple and economical solution for transmitting the relative audio signals to the electromagnetic transducer and the loudspeaker.

In a further aspect of the invention, the audio signal generator is connected to the loudspeaker by means of a second amplifier and a device for regulating the power of the signal amplified by the second amplifier.

This aspect of the invention advantageously enables the patient to regulate the sound volume generated by the loudspeaker to his or her taste, in a totally independent way with respect to the power of the pulsed magnetic field generated by the electromagnetic transducer.

Lastly, in a further aspect of the invention the device can further comprise a source of radio frequency waves suitable for emitting the radiofrequency waves at the opening of the depression chamber, such as to strike the surface of the body closing it.

This aspect of the invention has the advantage of applying, to the tissues, a radio-frequency treatment which obtains further benefits, among which the re-establishing of skin tone, the stimulation of the surface micro-circulation and the cellular exchange and the stimulation of the lymphatic system, which synergically superpose on the benefits obtainable with endodermic massage, magnetotherapy and music therapy.

BRIEF DESCRIPTION OF DRAWINGS

Further characteristics and advantages of the invention will emerge from a reading of the following description, provided by way of non-limiting example, with the aid of the figures illustrated in the accompanying tables of drawings.

BEST MODE FOR CARRYING OUT THE INVENTION

Figure 1:
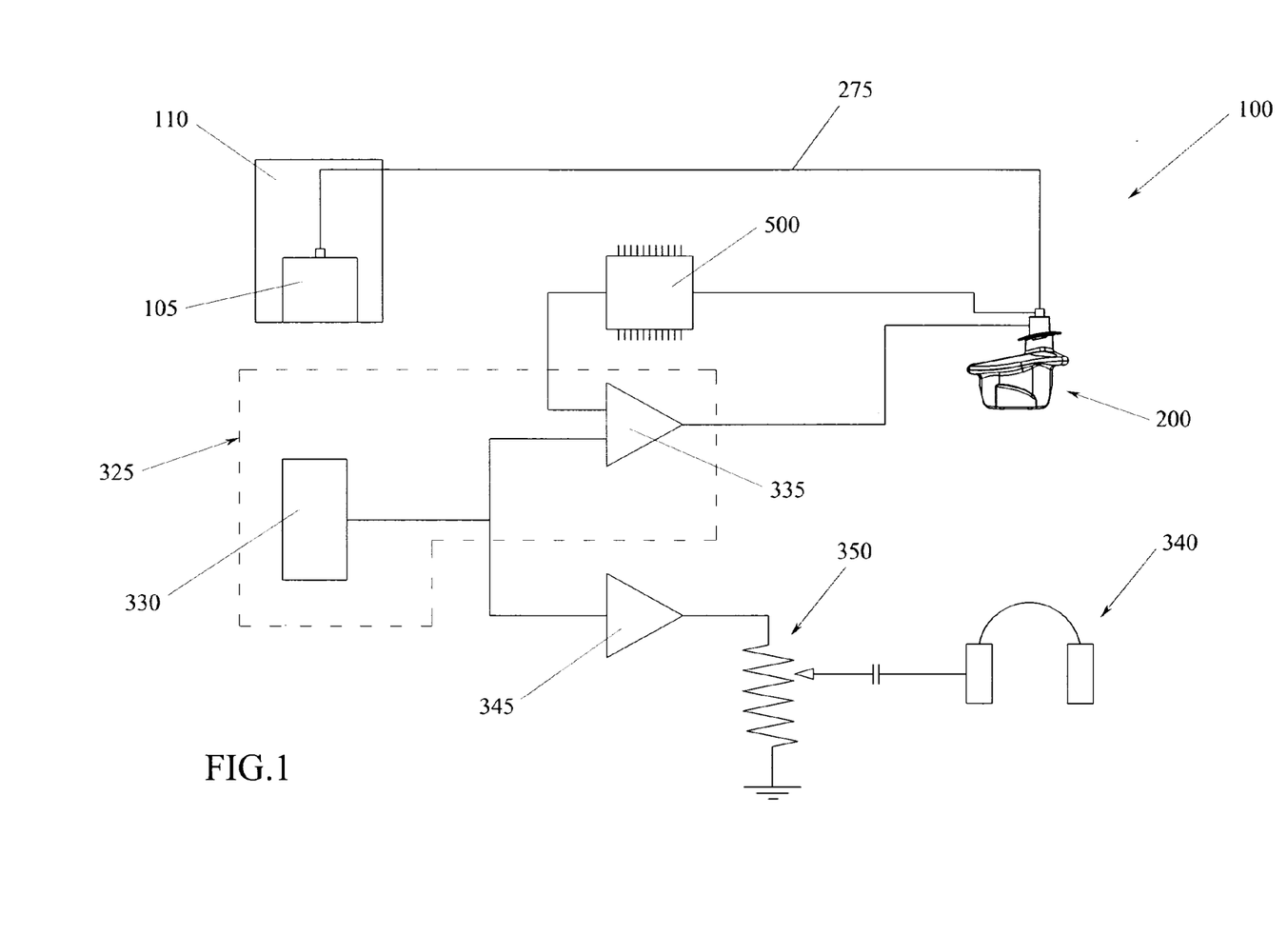
FIG. 1 is a diagram representing an electromedical device according to the invention.

FIG. 1 illustrates an electromedical device 100, which comprises an operating head 200, commonly also called hand-piece, which is suitable for gripping by an operator in order to be placed on the skin of a patient and move in correspondence with the areas to be treated.

Figure 2:
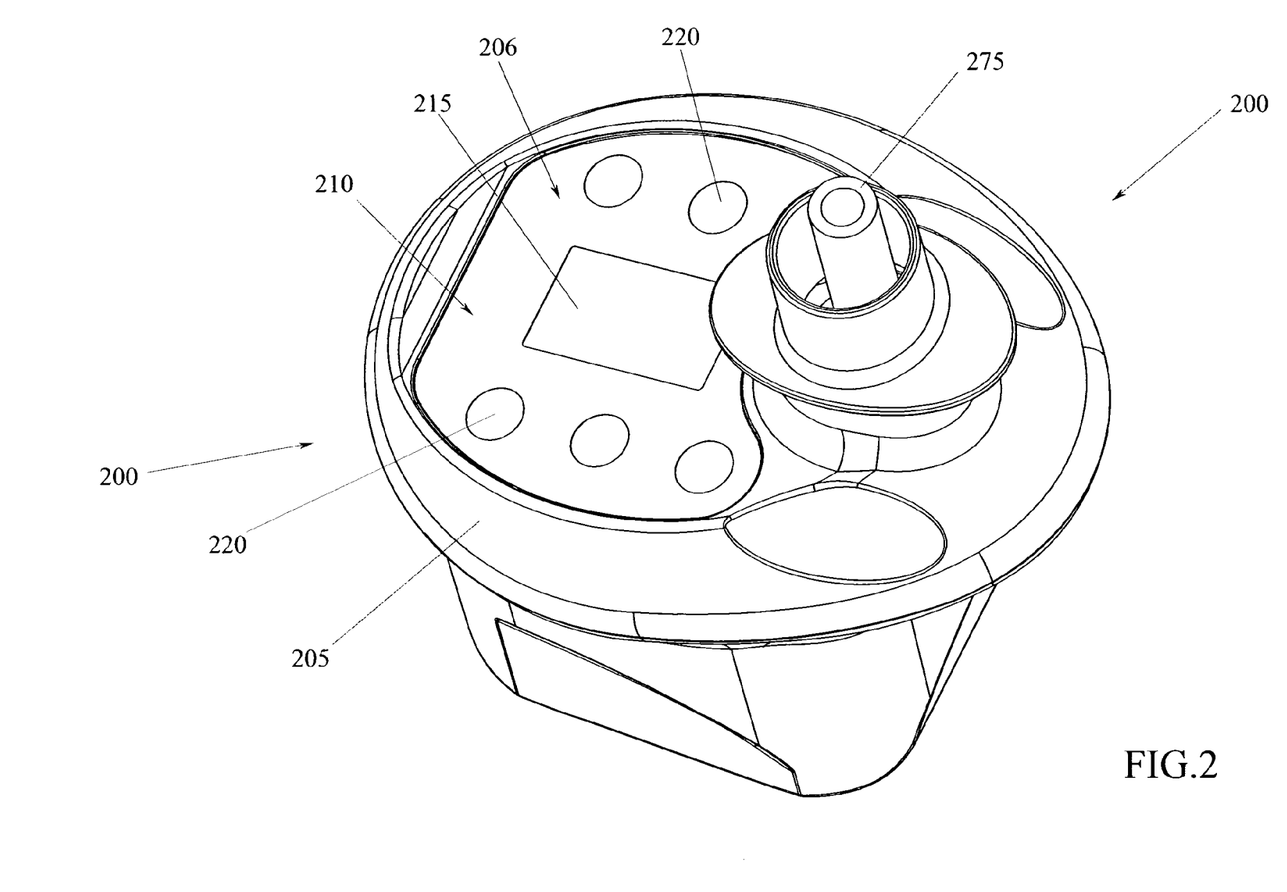
FIG. 2 is a perspective view from above of the operating head of the device of FIG. 1.
Figure 3:
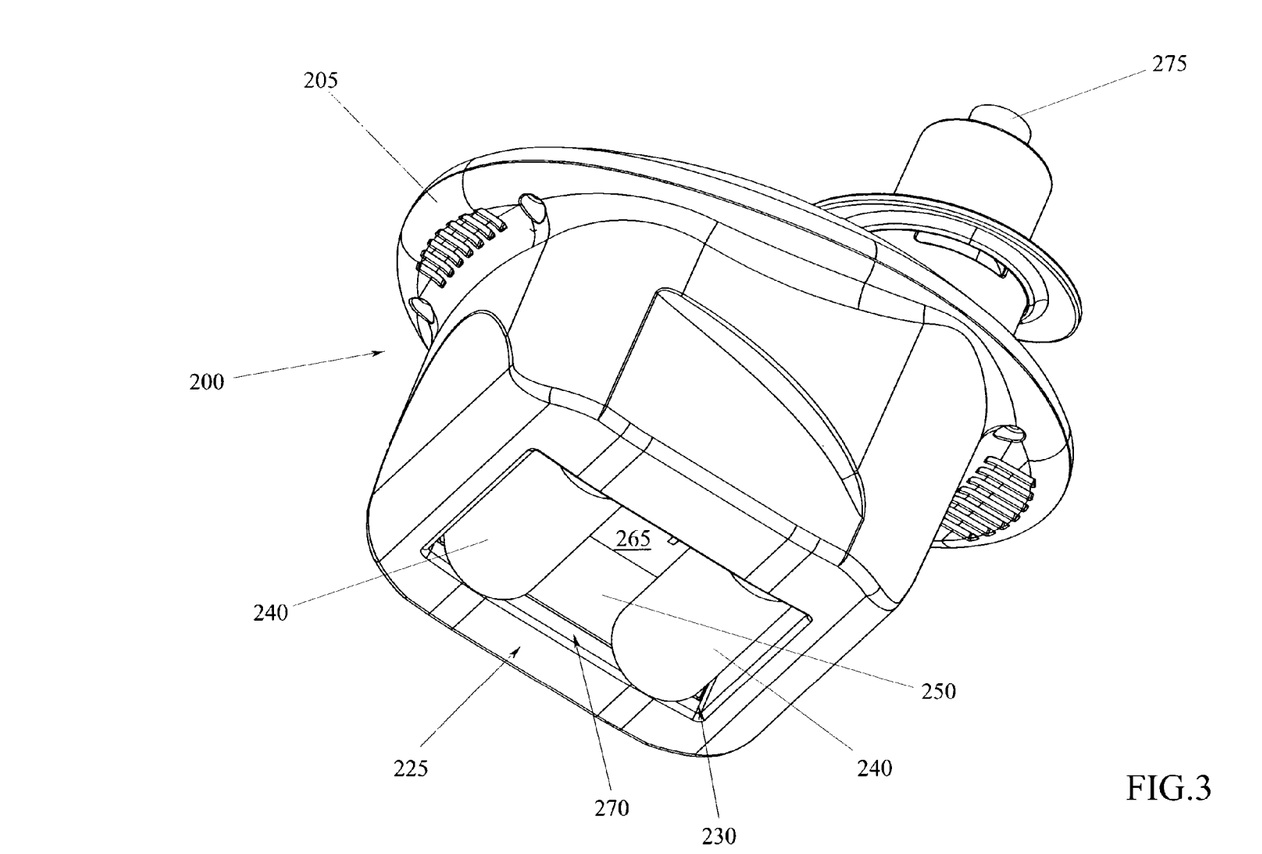
FIG. 3 is a perspective view from below of the operating head of FIG. 2.

As shown in FIG. 2, the operating head 200 comprises an internally hollow first casing 205, the external shape of which is ergonomically designed for easy gripping by the operator. The shape and dimensions of the outer casing 205 may also be different, depending for example on whether the operating head 200 is used for the treatment of more or less large areas of the body or face.

Figure 5:
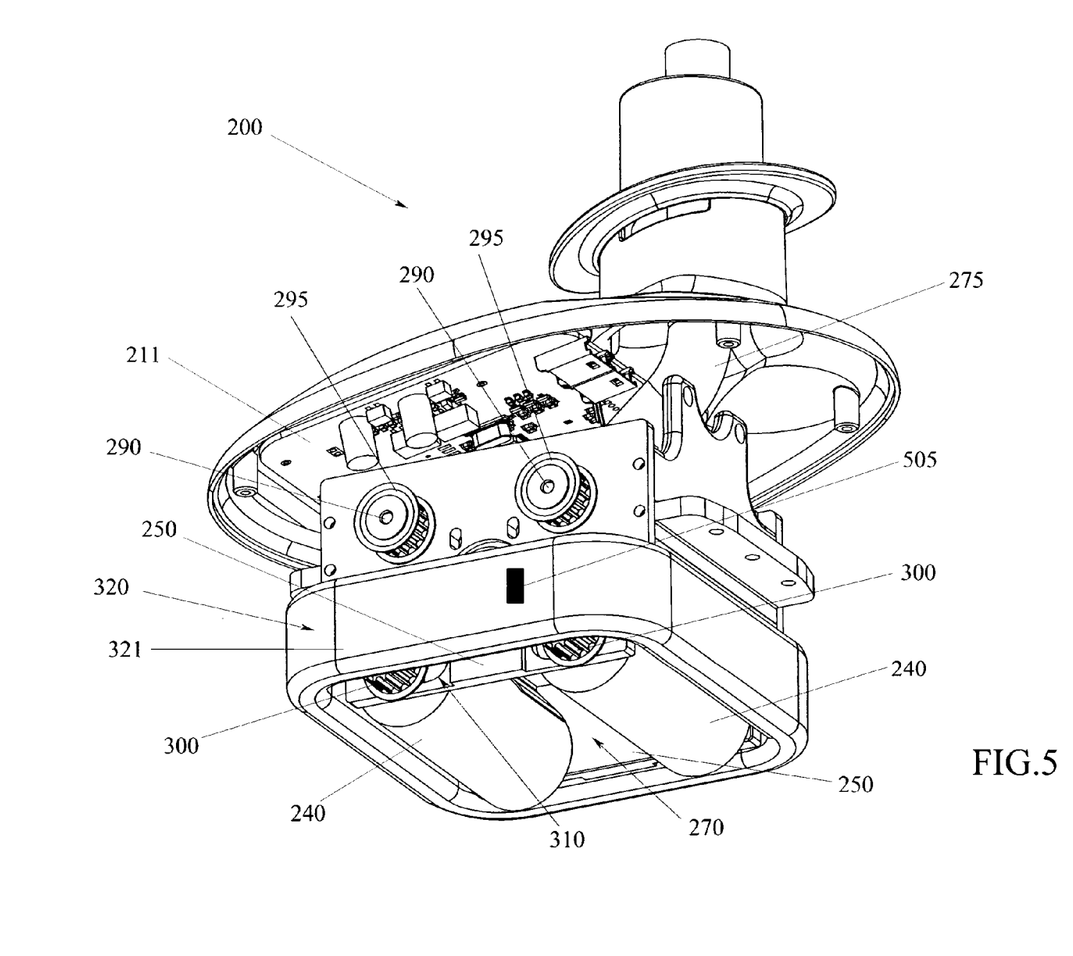
FIG. 5 is a perspective view from below of the operating head of FIG. 2, shown from a different angle to FIG. 3 and in which the lower part of the external casing has been removed to show some internal details.

Interface means 206 are positioned on the upper face 210 of the housing 205, which interface means 206 enable the operator to control the operation of the device 100. The interface means 206 are mounted and connected to an electronic card 211 which is mounted inside the casing 205 (see FIGS. 5 and 6). In the embodiment illustrated herein, the interface means 206 include a display 215 and a series of buttons 220. However, in other embodiments, the interface means 206 might be differently realized.

Figure 6:
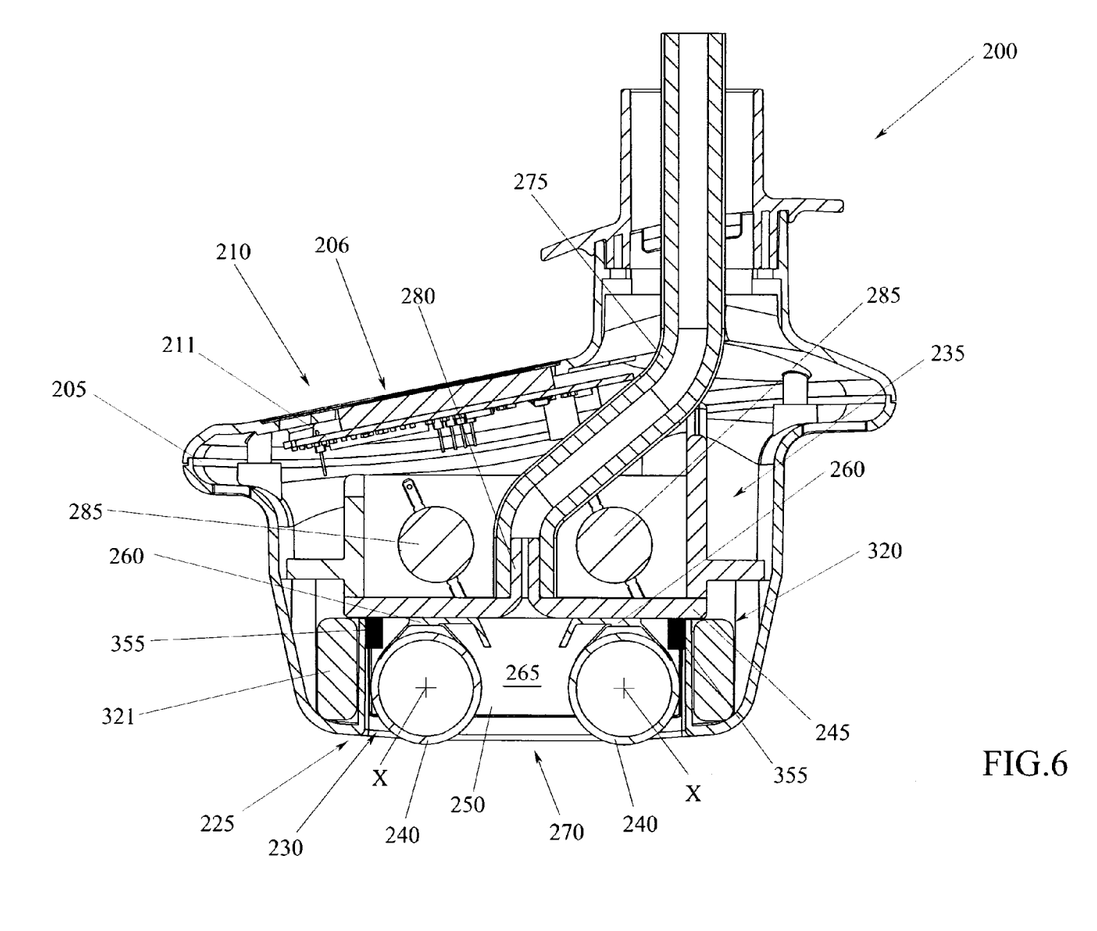
FIG. 6 is a section of the operating head of FIG. 2, carried out along a median vertical plane.

An opening 230 is afforded on the lower face 225 of the housing 205, in this case having a rectangular shape, through which access is afforded to the interior volume 235 of the casing 205. Two rollers 240 are mounted inside the opening 230, which are mutually parallel, opposite and mutually spaced, so that between them a passage is defined into the interior volume 235 of the casing 205. As shown in FIG. 6, the central axes X of the rollers 240 lie in a plane that is substantially parallel to the lower face 225 of the housing 205, and are positioned such that the lateral surface of each roller 240 protrudes with a limited portion to the outside through the opening 230. In the example illustrated here, the rollers 240 are identical to one another and are made of a metallic material, for example steel. However, in other embodiments, the rollers 240 may be of different sizes and/or be made of other materials, for example plastic or rubber.

Inside the casing 205, the rollers 240 are surmounted by a flat wall 245, substantially parallel to the central axes X, and are axially interposed between two side walls 250 that are oriented perpendicularly with respect to the flat wall 245. A section 260 having a flared, cross-section is interposed between the flat wall 245 and each roller 240, a concavity of which section is directed towards the central axis X, so that the inclined sides are resting on the lateral surface of the respective roller 240. Each section 260 extends longitudinally along the length of the roller 240, and is preferably made of rubber, so as to act substantially as a hermetic seal.

In this way, the rollers 240, the side walls 250, the flat wall 245 and the sections 260 overall delimit a depression chamber 265, which communicates with the outside only through the opening 270 bounded by the rollers 240 and by the side walls 250, the opening 270 being in fact a small portion of the opening 230 of the casing 205.

As schematically illustrated in FIG. 1, the depression chamber 265 is placed in communication with a vacuum pump 105, which is contained in a machine body 110 separated from the operating head 200. The communication is achieved through a conduit 275, typically a flexible conduit having an end connected with the suction of the vacuum pump 105 and the opposite end connected with a sleeve 280 fashioned in the flat wall 245 and leading to the depression chamber 265.

Figure 4:
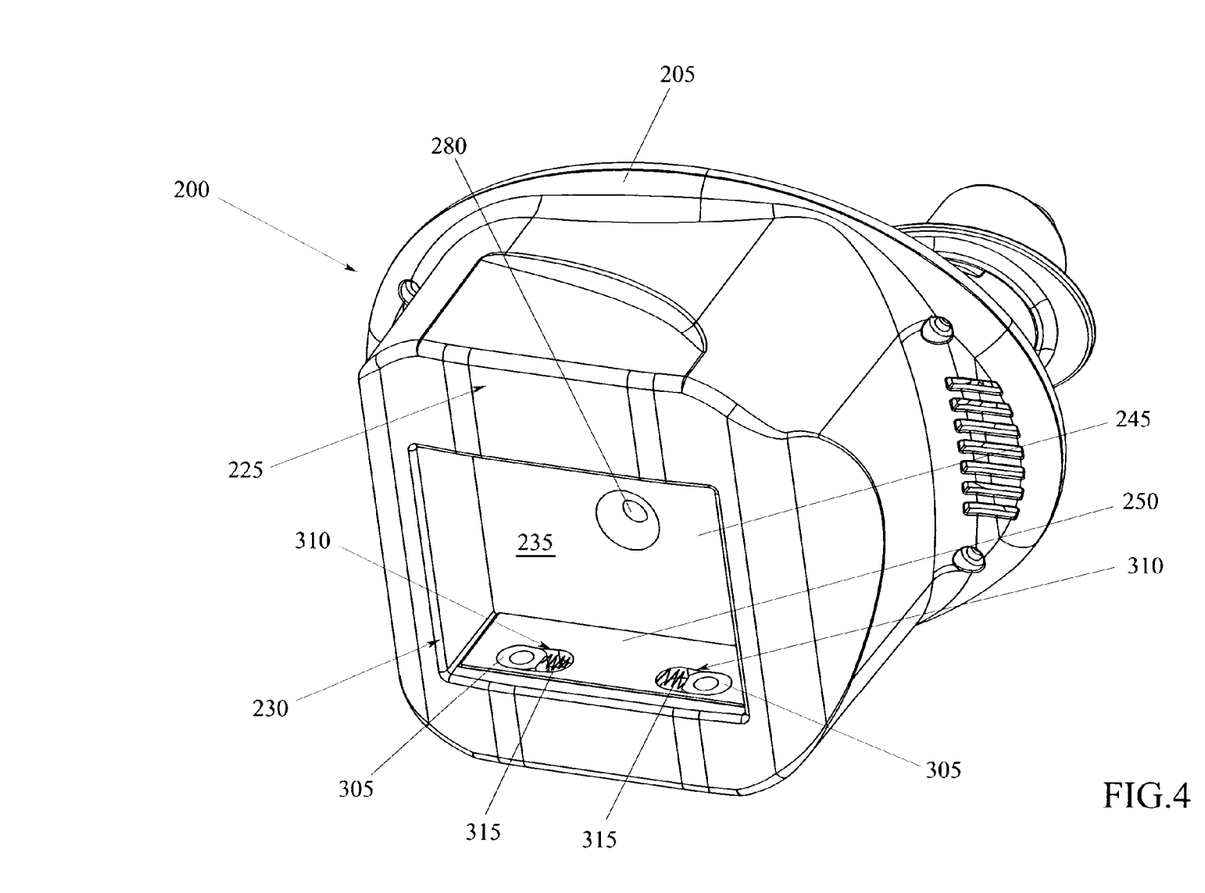
FIG. 4 is a perspective view from below of the operating head of FIG. 2, shown from a different angle with respect to FIG. 3 and wherein some elements have been removed in order to show some otherwise-hidden details.

Entering into more detail, each roller 240 is mounted via a respective coaxial shaft support (not visible), which projects for a certain distance from both ends of the roller 240. As shown in FIG. 4, each projecting portion of each central shaft is inserted inside a respective bushing 305, which in turn is slidably received in a respective slot 310 afforded in the side wall 250. The slots 310 develop in a substantially parallel direction to the plane of the central axes X of the rollers 240. In this way, each roller 240 is supported by the side walls 250 but is also mobile on them between a position of maximum distance and a position of minimum distance with respect the other roller 240. A small spring 315 is then accommodated in each slot 310, which spring 315 is destined to act on the bushing 305 so as to constantly push the roller 240 towards the respective maximum distance position. In other embodiments, the springs 315 could be replaced by other types of springs selected to perform the same function.

Two electric motors 285 (see FIG. 6) are installed inside the casing 205, above the flat wall 245, each of which motors 285 exhibits a rotating shaft 290 (see FIG. 5) that freely inserts in a hole (not visible) afforded in one of the side walls 250, such as to protrude from the opposite side where it is keyed to a cogged pulley 295. Each cogged pulley 295 is connected to a respective further cogged pulley 300, via a respective cogged belt (not shown since of usual type). Each of these additional cogged pulleys 300 is in turn keyed to one end of the central shaft of a respective roller 240. In this way, each roller 240 is destined to be set in rotation around its central axis X by a respective electric motor 285. Note that in other embodiments a single electric motor may be provided, connected such as to actuate both rollers 240.

The electric motors 285 can be turned on and off directly by an operator or by the patient, using appropriate manual controls that can be included between the interface means 206 associated to the operating head 200 or which can be positioned on the machine body 110.

In the example illustrated herein, the electric motors 285 and the related transmission systems are configured so that the rollers 240 rotate around the respective central axes X in the same direction and at the same speed. It is not excluded, however, that in other embodiments, the rollers 240 can be rotated at different speeds and/or in opposite directions. The device 100 might even include means for adjusting the speed and/or the rotation direction of the rollers 240.

An electromagnetic transducer 320 is also installed in the housing 205. In the embodiment illustrated herein, the electromagnetic transducer is defined by a coil 321 of electrically conductive cable, which is wound around the rollers 240 and the side walls 250, so that its central axis is substantially perpendicular to the plane central axis X of the roller 240. In other words, the coil 321 is positioned within the housing 205 right by the opening 230, so that its plan extension surrounds the opening 230. The coil 321 constitutes an electromagnetic inductance, which is destined to generate a magnetic field proportional to the current that runs through it.

To this end, as schematically illustrated in FIG. 1, the electromagnetic transducer 320 is connected to a generator of pulsed electric current, generally denoted by 325, so that when the coil 321 is crossed by the pulsed current, it generates a pulsed magnetic field in the zone where the rollers 240 are located.

In the example illustrated herein, the generator 325 includes an audio generator 330, and an amplifier 335 (or electric amplification circuit), which is connected to the audio generator 330 and the electromagnetic transducer 320, such as to amplify a sound signal generated by the generator 330 and transmit the amplified audio signal to the coil 321.

It is specified that the term audio signal relates to an electrical signal representing a sound having a more or less complex harmonic content.

The audio generator 330 can be any device suitable for reproducing a previously recorded and/or synthesized audio signal which is then stored on a support. This support can be either physical, such as a CD, or a multi-media file, such as an mp3 file. Consequently, the audio generator 330 may be an ordinary CD player or a media player. The audio generator 330 can be integrated into the machine body 110, or it can be a separate device.

The amplifier 335 may in turn be integrated into the operating head 200, for example in the electronic card 211, or can be a separate device and be installed, for example, inside the machine body 110.

The audio signal transmitted by the generator 330 to the electromagnetic transducer 320 is preferably a complex audio signal, comprising an audio signal superposed on a pulsed stochastic audio signal. In this way, the electromagnetic transducer 320 will be able to generate a pulsed magnetic field having the same frequency as the pulsed audio signal, and a stochastic magnetic field which follows the course of the stochastic audio signal and which superposes on the pulsed magnetic field.

In particular, the aforementioned audio signal complex may be formed by two waveforms, of which a first waveform modulated by the second waveform.

The first waveform can be a square wave, while the second waveform can be a stochastic signal obtained from a musical composition. This musical composition is preferably a piece by Mozart, possibly modified to enhance certain specific frequencies, such as the cyclotron resonance frequencies of elements such as Li, Na, K and Ca. Even more preferably, the musical composition used is the Mozart's K448 concert.

The device 100 further comprises an electronic processor 500. The electronic processor 500 is connected with the amplifier 335 and is programmed to adjust the power of the audio signal amplified by the amplifier 335. In particular, the electronic processor 500 may be configured to adjust the power of the audio signal based on the temperature of the coil 321 of the electromagnetic transducer 320, so that the coil 321 does not become too hot. To this end, the processor 500 is connected to a temperature sensor 505 (shown schematically in FIG. 5), such as an NTC sensor, which is located in the operating head 200 such as to be able to measure the temperature of the coil 321. The processor may also be connected to the audio generator 330 and/or to the electric motors 285 and/or to the depression pump 105, so as to control the respective operation. The processor 500 can be installed in the operating head 200, for example on the electronic card 211, or in the machine body 110.

The audio generator 330 is further connected to a speaker or a speaker system 340, which is suitable for transforming an audio signal generated by the generator 330 into an audible sound for the patient. In the example illustrated herein, the speaker system comprises an audio headset. In other embodiments, the speaker system may comprise a pair of earphones or other devices. In particular, the speaker system 340 is connected to the audio generator 330 via a second amplifier 345 (or second electric amplification circuit) destined to amplify the audio signal generated by the generator 330, and by a device 350 for adjusting the power of the amplified audio signal from the second amplifier 345, or for adjusting the sound volume generated by the speaker system 340.

The second amplifier 345 can be integrated into the operating head 200, for example in the electronic card 211, or can be a separate device and be installed, for example, inside the machine body 110.

The adjustment device 350 can be controlled directly by the operator or by the patient, using appropriate manual controls also predisposed in the machine body 110 or in the operating head 200, for example included in the interface means 206.

The audio signal transmitted from the generator 330 to the speaker system 340 is preferably a signal representing a musical composition, the original harmonic components of which can be optionally modified such that at least a part of them has a frequency of between 16 and 22 KHz, with the aim of obtaining an effective "Tomatis effect". The musical composition used in this ease too is preferably a composition by Mozart, in particular the K448 concerto.

More specifically, in the embodiment illustrated herein the audio generator 330 is a multi-channel audio generator, for example stereophonic, and one of the audio channels, for example the R channel, is connected to the electromagnetic transducer 320 while the other channel, for example the L channel, is connected to the loud-speaker system 340. Naturally, this solution assumes that the complex audio signal reproduced by the audio generator 330 has been previously recorded and/or synthesized, so that the R-channel carries the audio signal previously described for the electromagnetic transducer 320, and the L channel carries the signal previously described for the audio speaker system 340.

The device 100 can further comprise one or more electrodes 355 (shown schematically only in FIG. 6), embodied for example by studs of metal material, which are connected with a generator of radio frequency electromagnetic waves. The generator is accommodated in the machine body 110, while the electrodes 355 are mounted in the operating head 200, for emitting said radio frequency electromagnetic waves at the opening 270 of the vacuum chamber 265.

In use, the operating head 200 is applied on the patient, so that the rollers 240 rest directly on the skin and therefore the opening 270 of the depression chamber 265 is completely closed by a surface of the body. In this configuration, the depression chamber 265 is hermetically closed, so that the depression pump 105 may be activated in order to generate an aspiration or suction effect which creates a certain degree of depression inside the depression chamber 265, i.e. an internal pressure lower than the external pressure. This degree of depression causes the skin surface closing the depression chamber 265 to be slightly raised between the two rollers 240, forming a fold similar to what is created by the hand of a masseur during a massage.

Since the rollers 240 are mounted mobile, when the fold is formed, they near one another in contrast with the springs 315, such as to follow and accompany the movement of the patient's skin. This mutual approach has the advantage of preventing the rollers 240 from dragging on the skin, causing pain or at least some discomfort for the patient.

At this point, the operating head 200 can be displaced on the body of the patient, so that this displacement, together with the formation of the fold, creates a massaging action known as endomassage or endodermal massage. The endodermal massage generates an effect similar to that of a drainage massage or a lymphatic massage, which is very effective for facilitating the dissolving of fatty deposits and stimulating lymphatic circulation. Further, the negative pressure exerted by the suction, together with the positive pressure exerted by the rollers 240 and by the displacement of the device 100 over the body, create a mechanical stimulation which affects the anatomical structures underlying the fold, the main effects of which are to obtain a restructuring of the connective tissue, a proliferation of chondrocytes in the cartilage, increased blood profusion, blood flow and venous return, and an increase in the number of fibroblasts.

The electric motors 285 can be activated simultaneously to rotate the rollers 240. Rotating in the same direction, the rollers 240 facilitate the movement of the operating head 200 on the skin of the patient, reducing the friction that could cause pain or discomfort. At the same time, the rotation of the rollers 240 also facilitates the formation of the fold and improves the massaging action.

The audio generator 330 can be activated at the same time, so that the electromagnetic transducer 320 generates the pulsed magnetic field, possibly superimposed on the stochastic magnetic field. As it crosses the opening 270 of the depression chamber 265, the flow of said magnetic field also passes through the fold and the underlying areas of the body, obtaining an effective magnetotherapy treatment.

In other words, the electromagnetic transducer (320) is configured such that the flow of the pulsed magnetic field crosses the opening (270) of the depression chamber (265), in such a way to perform a magnetotherapy treatment.

The effectiveness of the magnetotherapy treatment is then particularly enhanced by the choice of the audio signal that generates the magnetic field, as described above.

The audio generator 330 can also simultaneously transmit the music signal to the speaker system 340, so that the patient also enjoys an effective music therapy treatment. The effectiveness of the magnetotherapy treatment is particularly enhanced by the choice of the musical piece, as described above.

At the same time, the source 355 can be activated by radio frequency waves. On crossing the opening 270 of the depression chamber 265, the radio frequency waves strike the fold and the surrounding areas of the skin of the patient, subjecting it to a radio frequency treatment which affords additional benefits, including the restoration of skin tone, stimulation of surface microcirculation and the cellular exchange and stimulation of the lymphatic circulation, which will superpose synergically in the benefits obtained with the endodermal massage, magnetic therapy and music therapy.

Obviously an expert in the sector might make numerous modifications of a technical-applicational nature to the device 100, without its thereby forsaking the ambit of the invention as claimed below.

The invention claimed is:

1. An electromedical device, comprising:
   an operating head comprising an internally hollow casing provided with an interior volume and having a lower face, wherein a first opening is afforded on the lower face and, through said first opening, access is afforded to the interior volume of the casing;
   a depression chamber placed in the interior volume of the casing and provided with a second opening;
   a suction source connected to the depression chamber;
   a pair of rollers mounted inside the first opening of the casing and at least partly delimiting the second opening of the depression chamber, wherein the second opening is a reduced part of the first opening of the casing;
   at least a motor means suitable for rotating the rollers;
   a generator of pulsed electric current; and
   an electromagnetic transducer connected to the generator to transform the pulsed electric current into a pulsed magnetic field, the electromagnetic transducer being configured such that a flow of the pulsed magnetic field crosses the opening of the depression chamber, in such a way to perform a magnetotherapy treatment;
   wherein the electromagnetic transducer is a coil of electrically conductive cable, wherein the coil is wound around the rollers and is positioned within the casing adjacent to the first opening, so that of the coil surrounds the first opening.

2. The device of claim 1, wherein the at least a motor means is configured to rotate the rollers in a same direction.

3. The device of claim 1, wherein at least one roller of the pair of rollers is mounted mobile in such a way as to be able to vary a distance between each roller in the pair of rollers, at least a spring being provided for maintaining the at least one mobile-mounted roller in a position of maximum distance between each roller in the pair of rollers.

4. The device of claim 1, wherein the generator of pulsed electric current comprises an audio generator, and an amplifier connected to the audio generator and to the electromagnetic transducer, to amplify an audio signal generated by the audio generator and transmit the amplified audio signal to the electromagnetic transducer.

5. The device of claim 4, wherein the audio signal transmitted to the electromagnetic transducer comprises a pulsed audio signal superposed on a stochastic audio signal.

6. The device of claim 4, comprising a processor connected to the amplifier for regulating the a power of the audio signal amplified by the amplifier.

7. The device of claim 6, comprising a temperature sensor suitable for measuring a temperature of the electromagnetic transducer, the temperature sensor being connected to the processor, which is configured to regulate the power of the amplified audio signal from the amplifier, according to a measured temperature of the temperature sensor.

8. The device of claim 4, wherein the audio generator is further connected to at least a loudspeaker for transforming an audio signal generated by the audio generator into an audible sound.

9. The device of claim 8, wherein the audio signal transmitted to the at least a loudspeaker comprises harmonic components having a frequency comprised between 16 and 22 KHz.

10. The device of claim 8, wherein the audio generator is a multi-channel audio generator, which is connected with the electromagnetic transducer and with, the at least a loudspeaker in such a way that a first audio channel is transmitted to the electromagnetic transducer and a second audio channel is transmitted to the at least a loudspeaker.

11. The device of claim 8, wherein the audio generator is connected to the at least a loudspeaker by means of a second amplifier and a device for regulating the power of the signal amplified by the second amplifier.

12. The device of claim 1, comprising a source of radio frequency waves suitable for emitting the radiofrequency waves at the second opening of the depression chamber.

13. The device of claim 1, wherein the operating head comprises:
   two side walls placed inside the casing, wherein the rollers are axially interposed between the two side walls,
   a flat wall, which is placed inside the casing, and surmounts the rollers,
   two sections, each of which has a flared cross-section and is interposed between the flat wall and the respective roller, wherein each section is provided with a concavity directed towards the respective roller, and has inclined sides resting on a lateral surface of the respective roller, wherein each, section extends longitudinally along a length of the respective roller;
   wherein the rollers, the side walls, the flat wall and the sections overall, delimit the depression chamber, which communicates with the outside only through the second opening bounded by the rollers and by the side walls.

* * * * *